US010172053B2

(12) United States Patent
Ando (10) Patent No.: US 10,172,053 B2
(45) Date of Patent: *Jan. 1, 2019

(54) RADIOGRAPHIC IMAGE CAPTURING SYSTEM

(71) Applicant: Konica Minolta, Inc., Tokyo (JP)

(72) Inventor: Takanori Ando, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/950,361

(22) Filed: Apr. 11, 2018

(65) Prior Publication Data

US 2018/0234899 A1  Aug. 16, 2018

Related U.S. Application Data

(63) Continuation of application No. 15/414,910, filed on Jan. 25, 2017, now Pat. No. 9,973,988.

(30) Foreign Application Priority Data

Feb. 16, 2016 (JP) ................................. 2016-026571

(51) Int. Cl.
| | |
|---|---|
| *H04W 36/20* | (2009.01) |
| *H04W 36/36* | (2009.01) |
| *H04W 36/06* | (2009.01) |
| *A61B 6/00* | (2006.01) |
| *H04W 84/12* | (2009.01) |

(52) U.S. Cl.
CPC ........... *H04W 36/06* (2013.01); *A61B 6/4405* (2013.01); *A61B 6/461* (2013.01); *A61B 6/465* (2013.01); *A61B 6/467* (2013.01); *A61B 6/563* (2013.01); *H04W 36/20* (2013.01); *H04W 36/365* (2013.01); *H04W 84/12* (2013.01)

(58) Field of Classification Search
CPC ............................. A61B 6/563; H04W 36/20
USPC ......... 455/550.1, 67.11, 566, 556.1; 348/308
See application file for complete search history.

(56) References Cited

U.S. PATENT DOCUMENTS

| 6,396,253 B1 * | 5/2002 | Petrick | .................. | H04N 5/367 324/522 |
| 2014/0169529 A1 * | 6/2014 | Hawver | .................. | H05G 1/56 378/116 |
| 2014/0347536 A1 * | 11/2014 | Senda | .................. | H04N 5/3741 348/308 |

FOREIGN PATENT DOCUMENTS

JP 2015058077 A 3/2015

* cited by examiner

*Primary Examiner* — John J Lee
(74) *Attorney, Agent, or Firm* — Lucas & Mercanti, LLP (57) ABSTRACT

A radiographic image capturing system includes: a radiographic image capturing apparatus which wirelessly transfers a signal value read from each of a plurality of radiation detecting elements; a channel switch controlling device capable of switching a channel used for wirelessly transferring the signal value from the radiographic image capturing apparatus to another channel; a notifying device which gives a notice to an operator who operates the radiographic image capturing system; and a display device which displays a radiographic image generated based on the signal value transferred from the radiographic image capturing apparatus, wherein the notifying device notifies an operator of the fact that the channel is being switched, at least once, while the radiographic image capturing apparatus is switching the channel.

8 Claims, 7 Drawing Sheets

| | | | | | | |
|---|---|---|---|---|---|---|
| L1 | D(1,1) | D(1,2) | D(1,3) | D(1,4) | D(1,5) | |
| L2 | D(2,1) | D(2,2) | D(2,3) | D(2,4) | D(2,5) | |
| L3 | D(3,1) | D(3,2) | D(3,3) | D(3,4) | D(3,5) | |
| L4 | D(4,1) | D(4,2) | D(4,3) | D(4,4) | D(4,5) | |
| L5 | D(5,1) | D(5,2) | D(5,3) | D(5,4) | D(5,5) | |
| L6 | D(6,1) | D(6,2) | D(6,3) | D(6,4) | D(6,5) | |
| L7 | D(7,1) | D(7,2) | D(7,3) | D(7,4) | D(7,5) | |
| L8 | D(8,1) | D(8,2) | D(8,3) | D(8,4) | D(8,5) | |
| L9 | D(9,1) | D(9,2) | D(9,3) | D(9,4) | D(9,5) | |
| L10 | D(10,1) | D(10,2) | D(10,3) | D(10,4) | D(10,5) | |
| L11 | D(11,1) | D(11,2) | D(11,3) | D(11,4) | D(11,5) | |
| L12 | D(12,1) | D(12,2) | D(12,3) | D(12,4) | D(12,5) | |

RADIOGRAPHIC IMAGE CAPTURING SYSTEM

CROSS REFERENCE TO RELATED APPLICATION

This application is a continuation of U.S. patent application Ser. No. 15/414,910, filed on Jan. 25, 2017, now U.S. Pat. No. 9,973,988, which claimed the priority of Japanese Application No. 2016-026571 filed on Feb. 16, 2016, the priority of both applications is claimed and the entire content of both applications are hereby incorporated by reference.

BACKGROUND OF THE INVENTION

Field of the Invention

The present invention relates to radiographic image capturing systems, in particular, to a radiographic image capturing system that transfers data from a radiographic image capturing apparatus through a wireless network.

Description of Related Art

Radiographic image capturing systems have been developed that capture radiographic images with radiographic image capturing apparatuses (flat panel detectors) each including multiple radiation detecting elements (see multiple radiation detecting elements 7 in FIG. 2, which will be described below). Each radiation detecting element generates electric charges in proportion to the dose of radiation emitted. The radiographic image capturing apparatus reads the electric charges as signal values. The radiographic image capturing system transfers the signal values read at the radiographic image capturing apparatus to a console which generates a radiographic image based on the signal values.

The signal values may be transferred from the radiographic image capturing apparatus to the console through a wired network, i.e., over a cable connecting the radiographic image capturing apparatus and the console, or through a wireless network.

For example, imaging is performed with the radiographic image capturing apparatus in an imaging room in a facility, for example, a hospital, or in a sickroom to which a medical cart equipped with the console and a radiation generating apparatus and the radiographic image capturing apparatus are moved, as described below. During the imaging, the radiographic image capturing apparatus and the console may be connected with a cable. Such a connection, however, may cause a radiological technician to stumble over the cable, precluding smooth imaging. To avoid this problem, the communication between the radiographic image capturing apparatus and the console is performed through a wireless network in many cases.

In recent years, much more opportunities are available to use wireless communications in medical equipment, in-hospital equipment, such as radiology information systems (RISs), or in-hospital networks. During a wireless transfer of the signal values from the radiographic image capturing apparatus to the console, as described above, such circumstances often cause interference between the transfer of the signal values and wireless communications from other equipment in a channel used to transfer the signal values.

For example, Japanese Patent Application Laid-Open Publication No. 2015-58077 discloses a radiographic image capturing system which identifies a wireless communication device that causes interference with signal values transmitted from a radiographic image capturing apparatus (referred to as an "electronic cassette" in this Patent Literature). If such a wireless communication device is identified, the radiographic image capturing system restricts the communications from the wireless communication device to prioritize the transfer of the signal values from the radiographic image capturing apparatus to the console. The restrictions of communication include, for example, stop of communications, restriction of the data rate (i.e., the volume of transferred data per unit time), and channel switching.

Actually, it is not so easy to restrict communications from other wireless communication devices to prioritize the wireless transfer of the signal values from the radiographic image capturing apparatus to the console in many cases, as described above. For example, IEEE802.11a, a wireless LAN standard, requires to avoid interference with radio waves from predetermined radar, such as a weather radar, through dynamic frequency selection (DFS), in other words, to take action to avoid interference with detected interference waves from radars.

Unfortunately, Japanese Patent Application Laid-Open Publication No. 2015-58077 cannot successfully restrict interference waves from a predetermined radar when such interference waves are detected during the wireless transfer of the signal values from the radiographic image capturing apparatus to the console, for example, over a 5 GHz band channel.

Many hospitals and other medical facilities preliminarily select non-overlapping channels in the 2.4 GHz or 5 GHz band and use these channels to perform wireless communications over a wireless LAN between in-hospital medical instruments or devices on in-hospital networks.

For example, during imaging in the imaging room in the hospital or the like as described above, various wireless communication devices other than the in-hospital medical equipment or those on the in-hospital networks may perform wireless communications over various channels in the vicinity of the imaging room. Despite the selection of channels used for communications between different medical instruments to avoid an overlap of channel frequencies, as described above, the channel frequencies for the medical instruments in the imaging room may overlap with those for wireless communication devices other than the medical instruments used in the vicinity of the imaging room, causing radio interference.

For example, during imaging in a sickroom to which the radiographic image capturing apparatus and a medical cart equipped with the console and the radiation generating apparatus are moved, as described above, another wireless communication device may also perform wireless communications in the sickroom or in the vicinity thereof over various channels. This situation may result in an overlap of channel frequencies between the medical instruments and another wireless communication device, resulting in radio interference.

In particular, these issues become more problematic when the medical cart equipped with the console is moved to different sites in a hospital for imaging. The channels used by wireless communication devices other than the medical equipment vary, depending on in-hospital places. This means that channels causing radio interference also vary, depending on in-hospital places. More specifically, a wireless transfer of signal values from the radiographic image capturing apparatus to the console over a particular channel in one in-hospital site (for example, a sickroom) may not cause radio interference, while a wireless transfer of the signal values over the same channel in the other site to which the medical cart is moved may cause radio interference with other wireless communication devices.

For example, during the transfer of the signal values from the radiographic image capturing apparatus to the console, the channel used to transfer the signal values may have radio interference with other wireless communication device. Such radio interference may require the channel used to transfer the signal values from the radiographic image capturing apparatus to the console to be switched to another channel. Such channel switching normally involves a temporary suspension of the transfer of the signal values for about one minute.

Unfortunately, a radiological technician may fail to notice such channel switching. Such a failure may hinder the operations of the radiological technician because the radiological technician does not know the reason why the transfer of the signal values is being suspended. The radiological technician may mistakenly believe that the cause of the suspension of the transfer lies in a defect of the system and perform an unnecessary operation or processing, which may prevent a proper implementation of operations.

SUMMARY OF THE INVENTION

An object of the present invention, which has been made to overcome the disadvantages of the conventional techniques described above, is to provide a radiographic image capturing system that provides an opportunity for a radiological technician to properly know that a channel used for a wireless transfer of signal values from the radiographic image capturing apparatus is under the switching operation.

To achieve the above object, a radiographic image capturing system in which one aspect of the present invention is reflected includes: a radiographic image capturing apparatus which wirelessly transfers a signal value read from each of a plurality of radiation detecting elements; a channel switch controlling device capable of switching a channel used for wirelessly transferring the signal value from the radiographic image capturing apparatus to another channel; a notifying device which gives a notice to an operator who operates the radiographic image capturing system; and a display device which displays a radiographic image generated based on the signal value transferred from the radiographic image capturing apparatus, wherein the notifying device notifies an operator of the fact that the channel is being switched, at least once, while the radiographic image capturing apparatus is switching the channel.

BRIEF DESCRIPTION OF THE DRAWINGS

The present invention will become more fully understood from the detailed description given hereinbelow and the appended drawings, and thus are not intended as a definition of the limits of the present invention, and wherein.

PREFERRED EMBODIMENT OF THE PRESENT INVENTION

With reference to the drawings, an embodiment of a radiographic image capturing system according to the present invention will now be described.

In the following description, the radiographic image capturing apparatus is of portable type and includes a sensor panel (not shown) having plural radiation detecting elements 7 two-dimensionally arranged thereon (see FIG. 2, which will be described below) in a housing 2 (see FIG. 1, which will be described below). Alternatively, the radiographic image capturing apparatus may be, for example, of a dedicated or stationary type having a sensor panel integrated with a supporting base.

Configuration of Radiographic Image Capturing Apparatus

The configuration of the radiographic image capturing apparatus will now be described. FIG. 1 is a perspective view of the radiographic image capturing apparatus. FIG. 2 is a block diagram illustrating an equivalent circuit of the radiographic image capturing apparatus. A radiographic image capturing apparatus 1 has a two-dimensional matrix of radiation detecting elements 7 (see FIG. 2) disposed on a sensor substrate (not shown) in a housing 2 (see FIG. 1).

Figure 1:
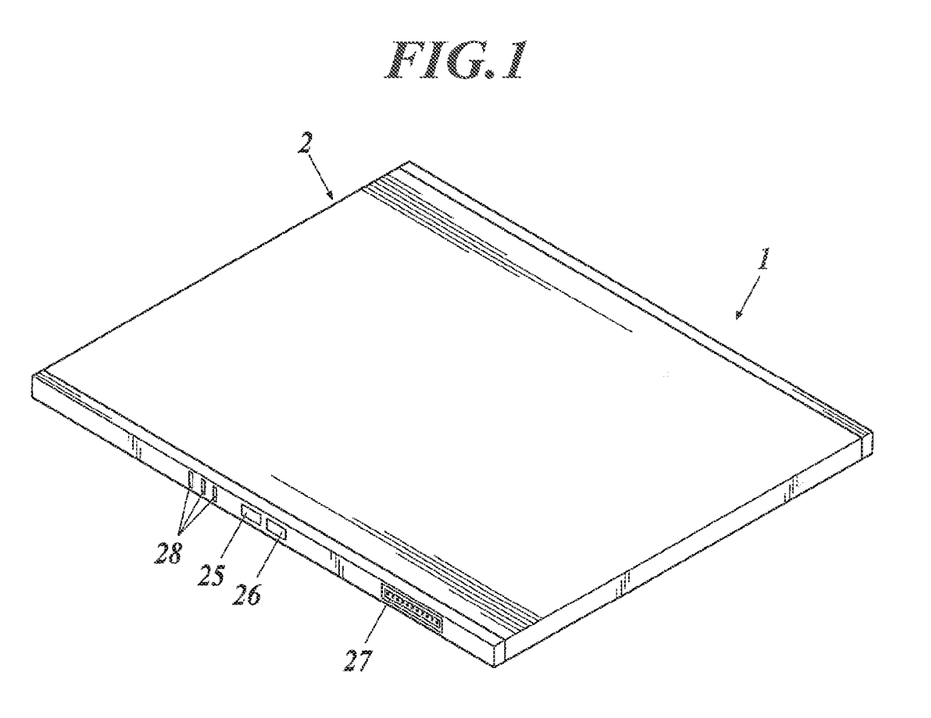
FIG. 1 is a perspective view of a radiographic image capturing apparatus.

With reference to FIG. 1, the radiographic image capturing apparatus 1 includes a power switch 25, a toggle switch 26, a connector 27, and an indicator 28 which are disposed on one side of the housing 2. The housing 2 is provided with an antenna 29 (see FIG. 2, which will described below) on, for example, the opposite side (not shown) of the housing 2 for wireless communications with an external device.

Figure 2:
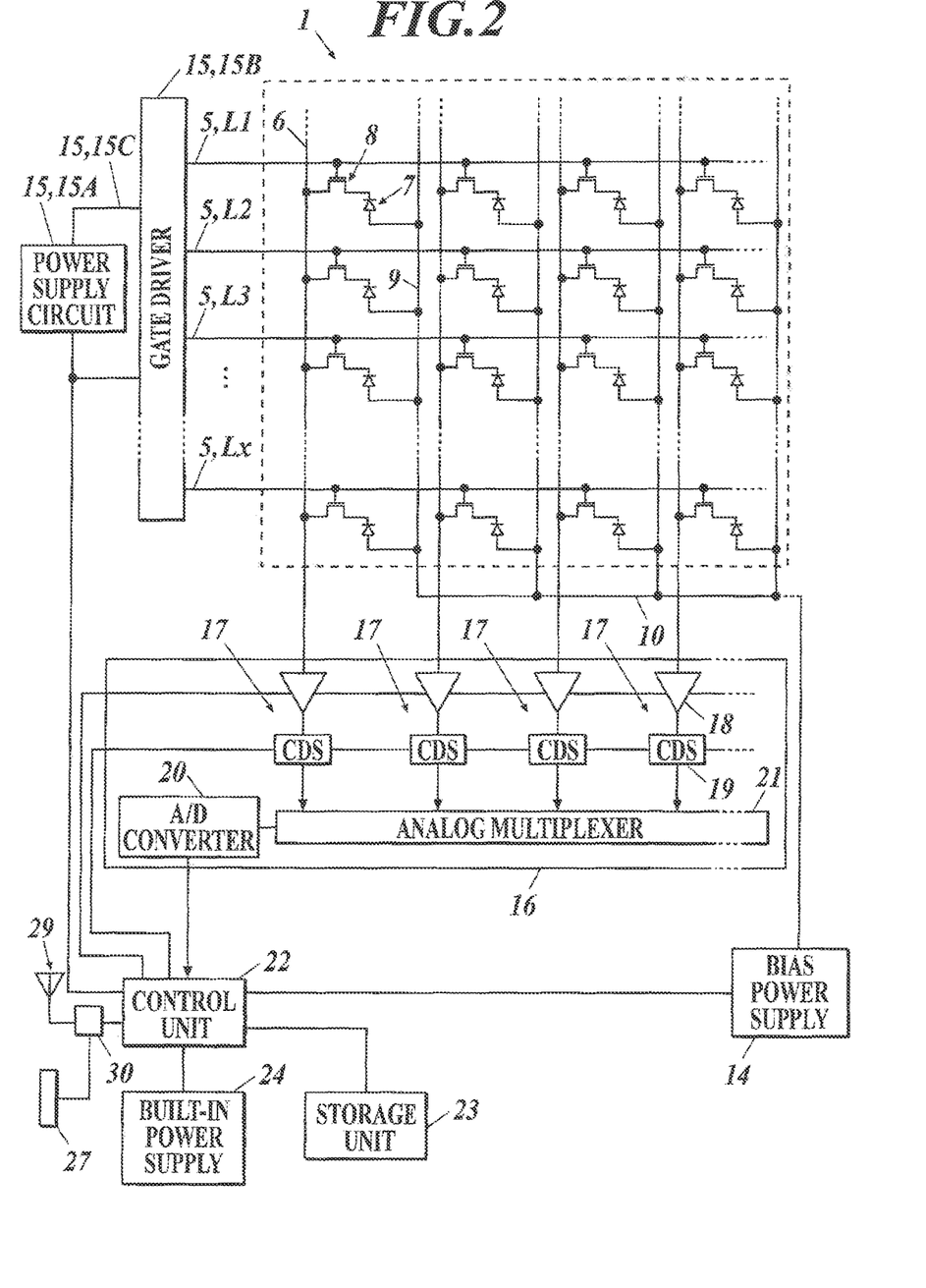
FIG. 2 is a block diagram illustrating an equivalent circuit of the radiographic image capturing apparatus.

As shown in FIG. 2, radiation detecting elements 7 are connected to bias lines 9. A bias power supply 14 applies a reverse bias voltage via the bias lines 9 and their connections 10 to the radiation detecting elements 7. The radiation detecting elements 7 are also connected to the respective thin film transistors (TFTs) 8, which function as switching elements. Each TFT 8 is connected to the corresponding signal line 6. The radiation detecting element 7 generates electric charges in proportion to the dose of the received radiation.

In a scan driving unit 15, on-stage voltage or off-state voltage is applied from a power supply circuit 15A to a gate driver 15B via a line 15C and then distributed to scanning lines 5(L1) to 5(Lx). The off-state voltage applied to each TFT 8 via the corresponding scanning line 5 puts the TFT 8 into the off-state, resulting in disconnection between the corresponding radiation detecting element 7 and the corresponding signal line 6 to accumulate electric charge in the radiation detecting element 7. In contrast, the on-state voltage applied to each TFT 8 via the corresponding scanning line 5 puts the TFT 8 into the on-state, resulting in the release of the electric charge accumulated in the corresponding radiation detecting element 7 to the corresponding signal line 6.

Each signal line 6 is connected to the corresponding readout circuit 17 in a readout IC 16. In order to read signal values D, the gate driver 15B sequentially applies the on-stage voltage to the scanning lines 5(L1) to 5(Lx). The on-stage voltage applied puts the TFTs 8 into the on-state, which causes the electric charges to flow from the radiation detecting elements 7 into the readout circuits 17 via the TFTs 8 and the signal lines 6. Each amplifying circuit 18 outputs a voltage value in proportion to the electric charge received.

Correlated double sampling circuits 19 (CDSs in FIG. 2) each read the voltage value output from the corresponding amplifying circuit 18 as an analog signal value D and sequentially send the analog signal value D to an A/D converter 20 via an analog multiplexer 21. The analog signal values D are sequentially converted into digital signal values D at the A/D converter 20 and the digital signal values are sequentially stored in a storage unit 23.

A control unit 22 may be a computer provided with a not-shown central processing unit (CPU), read only memory (ROM), random access memory (RAM) and input/output interface, each being connected to a bus. Alternatively, the control unit 22 may be a field programmable gate array (FPGA). Alternatively, the control unit 22 may include a dedicated control circuit.

The control unit 22 is connected to the storage unit 23, a built-in power supply 24, and a communication unit 30. The storage unit 23 includes a static RAM (SRAM), synchronous DRAM (SDRAM), or NAND flash memory. The built-in power supply 24 includes a lithium ion capacitor. The communication unit 30 is configured to communicate with an external device through a wireless or wired network via the antenna 29 or connector 27.

As described above, the control unit 22 controls the application of reverse bias voltage to each radiation detecting element 7 from the bias power supply 14, controls the operations of the scan driving unit 15 and the readout circuits 17 to read signal values D from radiation detecting elements 7 to store the read signal values in the storage unit 23, and transfers the stored signal values D to an external device through the communication unit 30.

After reading the signal values D from the radiation detecting elements 7, the control unit 22 of the radiographic image capturing apparatus 1 according to this embodiment extracts a predetermined portion of the read signal values D as signal values Dpre for preview, transfers the extracted signal values Dpre for preview to a console C prior to the other signal values D, and then transfer the other signal values D to the console C. Alternatively, the control unit 22 may transfer all the signal values D to the console C without extracting the signal values Dpre for preview.

Figure 3:
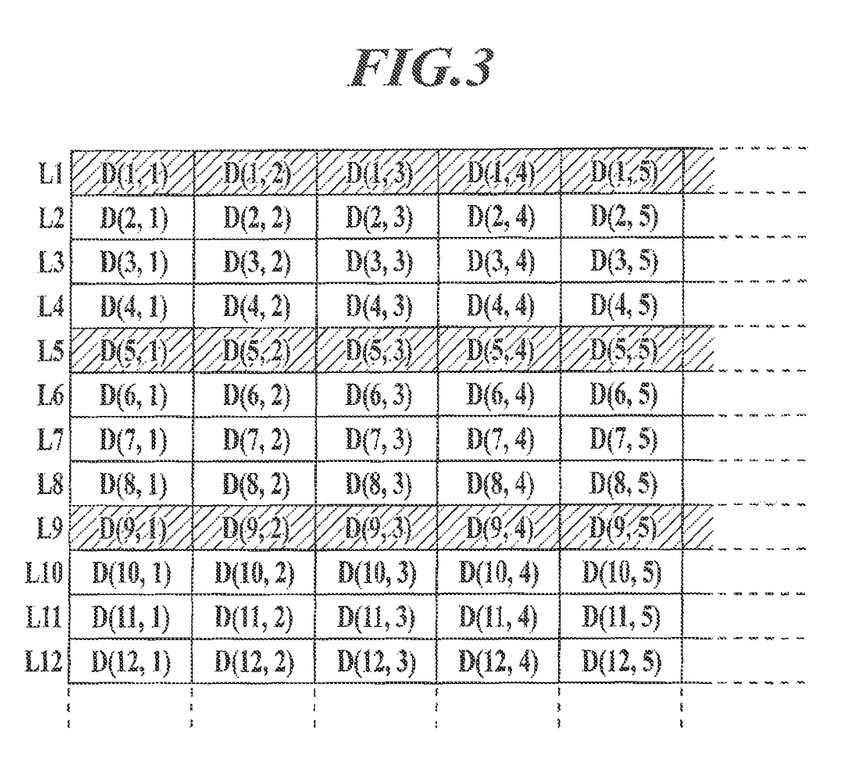
FIG. 3 illustrates exemplary extraction of signal values for preview.

For example, the signal values Dpre for preview (shaded portions) are extracted from all the read signal values D(n, m), as shown in FIG. 3: The signal values D(n, m) read from the radiation detecting elements 7 connected the scanning lines 5 may be extracted as signal values Dpre for preview every predetermined number of scanning lines 5 (four scanning lines in FIG. 3).

In FIG. 3, L1 and L2 represent scanning lines 5(L1) and 5(L2) in FIG. 2, respectively. D(n, m) represents a signal value D read from a radiation detecting element 7(n, m), which is at row "n" and column "m" in the matrix of radiation detecting elements 7. Alternatively, the signal values Dpre for preview may be extracted by any other scheme, for example, signal values Dpre for preview may be extracted every 3×3 or 4×4 matrix of radiation detecting elements 7 among the signal values D.

Radiographic Image Capturing System

Figure 4:
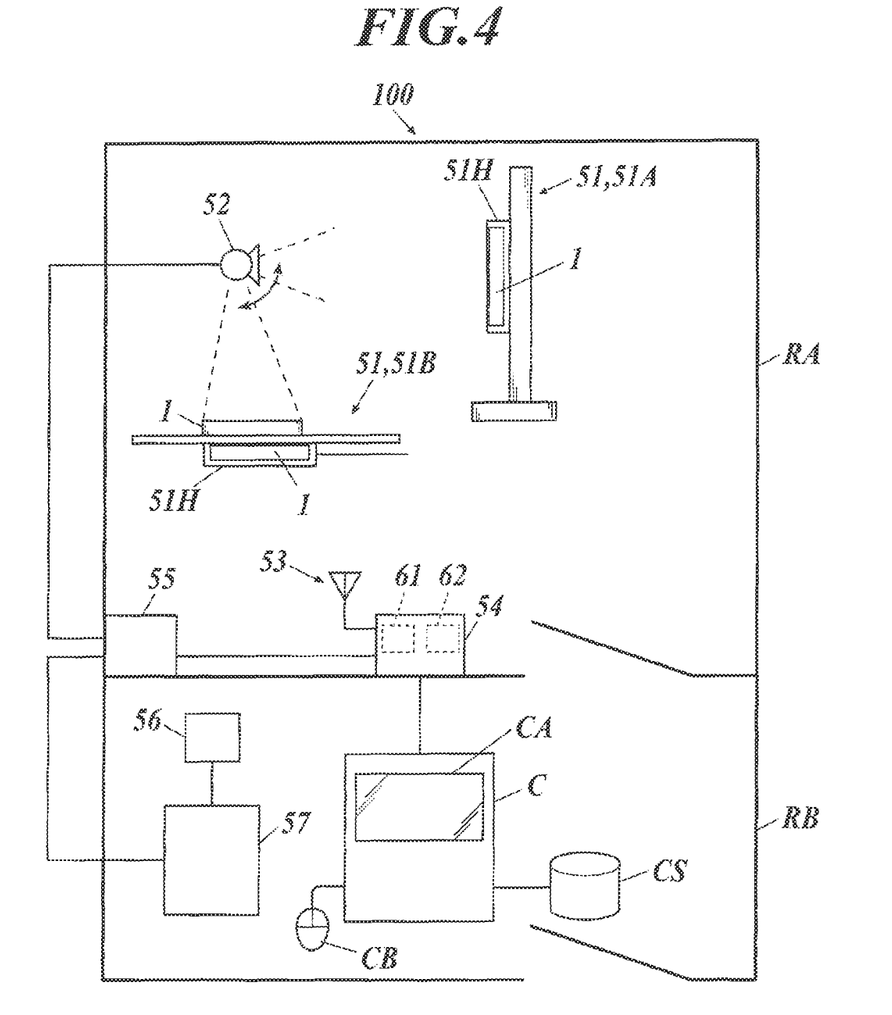
FIG. 4 illustrates an exemplary configuration of a radiographic image capturing system according to this embodiment.
Figure 5:
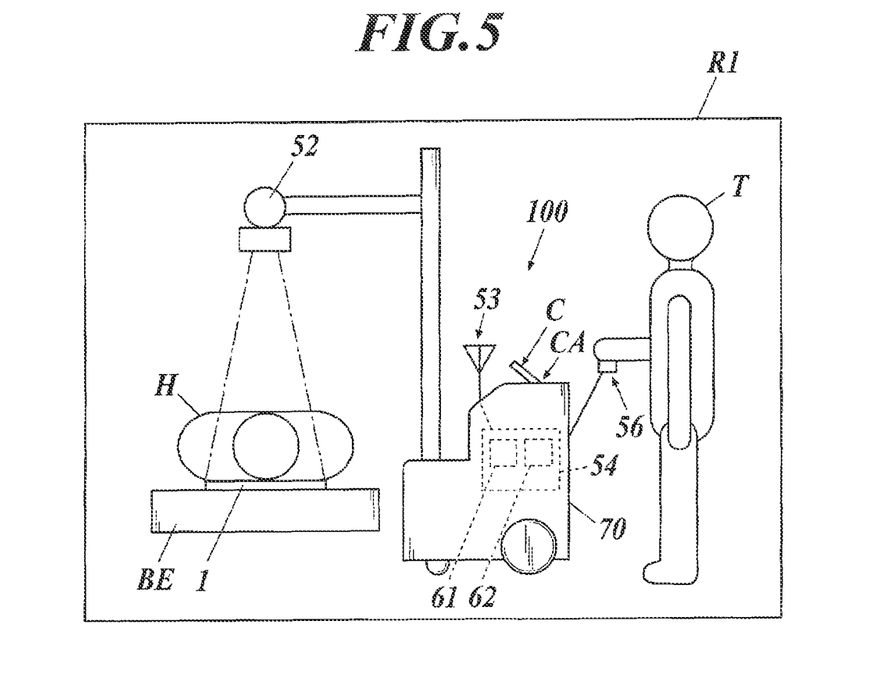
FIG. 5 illustrates another exemplary configuration of the radiographic image capturing system according to this embodiment.

A radiographic image capturing system 100 according to this embodiment will now be described. The radiographic image capturing system 100 may be installed in, for example, an imaging room RA and/or a front room RB, as shown in FIG. 4. Alternatively, the radiographic image capturing system 100 may be installed in a medical cart 70, as shown in FIG. 5.

For the radiographic image capturing system 100 installed in the imaging room RA and the like, the radiographic image capturing apparatus 1 may be placed in, for example, a cassette holder 51H of an imaging platform 51, as shown in FIG. 4. The imaging platform 51A in FIG. 4 represents an imaging platform used to image a standing subject. The imaging platform 51B represents an imaging platform used to image a lying subject. Alternatively, the radiographic image capturing apparatus 1 may be placed, for example, between a subject (not shown) lying on a top panel of the imaging platform 51B, which is used to image a lying subject, and the top panel.

The imaging room RA is provided with at least one radiation generating apparatus 52, which emits radiation toward the radiographic image capturing apparatus 1 through a subject (not shown). The imaging room RA is also provided with an access point 54 having an antenna 53. The access point 54 relays communications between devices inside and outside the imaging room RA through a wireless or wired network.

The communications between the radiographic image capturing apparatus 1 and the access point 54 according to this embodiment are performed through a wireless network between the antenna 29 (see FIG. 2) of the radiographic image capturing apparatus 1 and the antenna 53 (see FIG. 4) of the access point 54. The signal values D or the signal values Dpre for preview, which are transferred from the radiographic image capturing apparatus 1 to the console C through a wireless network, as described above, are received by the access point 54 and then sent to the console C from the access point 54.

The access point 54 according to this embodiment is provided with a channel interference detecting device 61 and a channel switch controlling device 62, which will be described below. The access point 54 is connected to a generator 55 of the radiation generating apparatus 52 and to the console C, and relays communications among the radiographic image capturing apparatus 1, the console C, and the generator 55 of the radiation generating apparatus 52.

The access point 54 is connected to in-hospital systems, such as RIS, a hospital information system (HIS) and a picture archiving and communication system (PACS), via a network (not shown). The network may partially include wireless communications.

The generator 55 of the radiation generating apparatus 52 controls the radiation generating apparatus 52 to emit radiation in a dose in proportion to an X-ray tube voltage, an X-ray tube current, or irradiation time (or mAs value) set by an operator or radiological technician.

The front room RB (also referred to as an operation room) is provided with an operator station 57 of the radiation generating apparatus 52. The operator station 57 is provided with an exposure switch 56 which is used by an operator, such as a radiological technician, to instruct the generator 55 to start emitting radiation. The front room RB is also provided with the console C with a built-in computer. The console C may be installed outside the imaging room RA and front room RB or in any other room.

The console C is provided with a screen CA of a cathode ray tube (CRT) or liquid crystal display (LCD) and is connected to an input unit CB, such as a mouse or a keyboard. The console C is also connected to a storage unit CS composed of a hard disk drive (HDD) or has a built-in storage unit CS.

In contrast, the radiographic image capturing system 100 may include the medical cart 70 on which the radiation generating apparatus 52 and the console C are mounted, as shown in FIG. 5. The medical cart 70 is moved to a sickroom R1 for imaging. In this case, the generator 55 of the radiation generating apparatus 52 (not shown in FIG. 5) and the access point 54 including the channel interference detecting device 61 and the channel switch controlling device 62 are housed in the main body of the medical cart 70.

In this case, the radiographic image capturing apparatus 1 is placed between a bed BE and a subject (patient) H, as shown in FIG. 5, or is applied to the body of the patient. In this case, an operator T, such as a radiological technician, also operates the exposure switch 56 to emit radiation from the radiation generating apparatus 52 to capture an image. After the capture, signal values Dpre for preview are transferred from the radiographic image capturing apparatus 1 to the console C through a wireless network.

Configuration of the Console C

Figure 6:
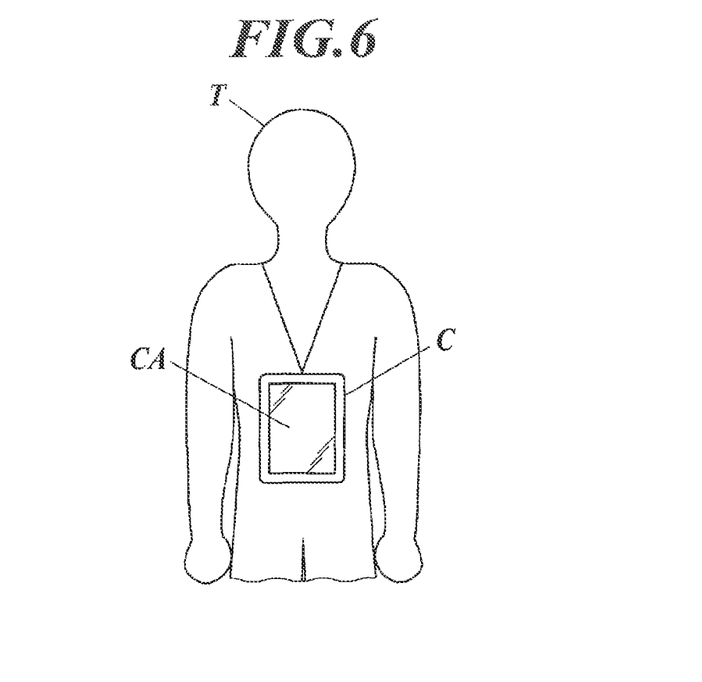
FIG. 6 illustrates a mobile terminal, carried by an operator, functioning as a console.

The console C may be a desk-top or note computer, as shown in FIGS. 4 and 5. Alternatively, the console C may be, for example, a mobile terminal, as shown in FIG. 6, which is carried by the operator T, such as a radiological technician. The console C mentioned in the following description may be a desk-top or note computer (see FIGS. 4 and 5) or a mobile terminal (see FIG. 6).

For the console C of a mobile terminal (see FIG. 6), communications between the access point 54 and the console C are performed through a wireless network. For the console C of a desk-top or note computer (see FIGS. 4 and 5), the communications between the access point 54 and the console C may be performed through a wireless or wired network.

The console C generates a radiographic preview image ppre (not shown) based on the transferred signal values Dpre for preview received from the radiographic image capturing apparatus 1 after imaging, and displays the generated radiographic preview image ppre on the screen CA. The operator T, such as a radiological technician, watches the radiographic preview image ppre appearing on the screen CA of the console C and determines the necessity for re-imaging.

The console C according to this embodiment functions as a display device that can display a radiographic image (the radiographic preview image ppre in the above case) generated based on the signal values transferred from the radiographic image capturing apparatus 1 (the signal values Dpre for preview in the above case). In the following description, the console C is referred to as the "display device C" when it functions as a display device. Alternatively, the display device may be separated from the console C.

After the reception of the signal values Dpre for preview, as described above, the console C receives the remaining signal values D (i.e., signal values D other than the signal values Dpre for preview) from the radiographic image capturing apparatus 1 and then reconstructs all the signal values D from the remaining signal values D and the signal values Dpre for preview. The console C performs image processing, such as gain correction, defective pixel correction, or gradation processing suitable for imaged portions, on the reconstructed signal values D to generate a radiographic image p (not shown). The console C according to this embodiment also displays the generated radiographic image p on the screen CA. The console C may omit display of the radiographic image p on the screen CA in some cases.

Radiographic Image Capturing System (Continued)

As described above, the radiographic image capturing system 100 according to this embodiment (see FIGS. 4 and 5) includes the radiographic image capturing apparatus 1, the display device C (the console C in this embodiment), the channel interference detecting device 61, and the channel switch controlling device 62. The processes to be performed in the channel interference detecting device 61, the display device C, and the channel switch controlling device 62 will now be described, together with the operation of the radiographic image capturing system 100 according to this embodiment.

For example, 2.4 GHz and 5 GHz bands each have multiple channels defined for wireless communications over a wireless LAN, as is well known. The channel interference detecting device 61 and the channel switch controlling device 62 according to this embodiment have non-overlapping frequency channels preliminarily defined for each band (channels 1, 6, 11, and 14 for 2.4 GHz band, for example). These channels are used for a wireless transfer of the signal values D (including the signal values Dpre for preview, the same applies hereinafter) from the radiographic image capturing apparatus 1.

Since channels for each band depend on countries, a list of channels available in a country in which the radiographic image capturing system 100 is used may be displayed on, for example, the screen CA of the display device C, although not shown in the drawing. A radiological technician may select one channel used for a wireless transfer of the signal values D from the radiographic image capturing apparatus 1 from the list. Information on the selected channel may be sent from the display device C to the channel interference detecting device 61 and/or the channel switch controlling device 62 to set the selected channel in the channel interference detecting device 61 and/or the channel switch controlling device 62.

The channel interference detecting device 61 can detect radio interference in a channel used for wireless communications at the access point 54. The channel interference detecting device 61 measures a radio interference level σ at each channel in use and detects the occurrence of radio interference at an observed radio interference level equal to or greater than a threshold σth, for example.

Upon detection of radio interference, the channel interference detecting device 61 according to this embodiment sends a signal indicating the detection of radio interference (hereinafter referred to as an "interference detection signal") to the display device C. The channel interference detecting device 61 may detect radio interference only for a channel reserved for use. Alternatively, the channel interference detecting device 61 may also detect radio interference for other channels.

Although the channel interference detecting device 61 may be separated from the access point 54, the channel interference detecting device 61 according to this embodiment is disposed at the access point 54, as shown in FIGS. 4 and 5 because the channel interference detecting device 61 detects radio interference at each channel used for wireless communications at the access point 54, as described above.

For example, a radio interference level σ, which is measured by the channel interference detecting device 61 for each channel, appears on the screen CA of the display device C so that the operator or radiological technician can confirm it, though the illustration thereof is omitted.

The channel interference detecting device 61 according to this embodiment can detect interference waves from predetermined radars, such as a weather radar (i.e., radio waves from predetermined radars required to avoid interference through DFS by IEEE802.11a, the same applies hereinafter) during detection of radio interference, as described above. Upon detection of interference waves from a predetermined radar, such as a weather radar, the channel interference detecting device 61 according to this embodiment sends a signal indicating the detection of interference waves from the radar (hereinafter referred to as a "DFS detection signal") to the display device C.

Upon reception of an interference detection signal or a DFS detection signal from the channel interference detecting device 61, the display device C sends an instruction signal for channel switching to the channel switch controlling device 62. In response to the switching signal, the channel switch controlling device 62 switches the channel used for a wireless transfer of the signal values D from the radiographic image capturing apparatus 1 to another channel.

Upon reception of the interference detection signal from the display device C, the channel switch controlling device 62 according to this embodiment, for example, instructs the channel interference detecting device 61 to send information on the radio interference level σ measured for each predetermined channel (or measure and send the radio interference level σ of each predetermined channel), and switches the current channel to another channel selected as having a lower radio interference level σ, for example, the lowest level, based on the information.

This configuration facilitates a wireless transfer of signal values D from the radiographic image capturing apparatus 1 since the post-switch channel has a lower radio interference level σ than that of the current channel. In the following description, the channel switch controlling device 62 switches the current channel to another channel with a lower radio interference level σ. Alternatively, for example, the channel switch controlling device 62 may switch the current channel to another channel in accordance with a predetermined priority.

The radiographic image capturing system 100 according to this embodiment is provided with a notifying device that gives notices to an operator of the radiographic image capturing system 100. In the following description, the notifying device is integrated with the display device C and sends a message to the screen CA of the display device C. Alternatively, the notifying device may make a sound with a speaker (not shown) or generate vibration with a vibrator (not shown) for notification.

Just like a notifying device configured to send messages, a notifying device configured to make a sound or generate vibration allows the operator to properly recognize that the channel is under the switching operation, for example, when the operator notices the sound or vibration. The notifying device may be separated from the display device C.

Upon reception of an interference detection signal from the channel interference detecting device 61, as described above, the display device C sends a switching signal to the channel switch controlling device 62. While a channel switch controlling device 61 is switching the channel as described above, the notifying device displays, for example, a message A1 "CHANNEL IS BEING CHANGED" on the screen CA of the display device C (see FIGS. 4 to 6), as shown in FIG. 7, to notify the operator or radiological technician that the channel is under the switching operation.

As described above, while the channel switch controlling device 62 is switching the channel used for a wireless transfer of the signal values D from the radiographic image capturing apparatus 1, the notifying device sends a message that the channel is under the switching operation. This configuration allows the operator or radiological technician to properly recognize that the channel is being switched.

As described above, it takes about one minute to switch a channel over the wireless LAN, for example. The message A1 "CHANNEL IS BEING CHANGED", as shown in FIG. 7, may appear together with a message A2 "CHANNEL CHANGE TAKES ABOUT ONE MINUTE", for example, indicating that the time t is required to switch the channel. This configuration allows the operator or radiological technician who watches the message A2 to properly recognize that it takes about one minute to switch the channel.

Figure 7:
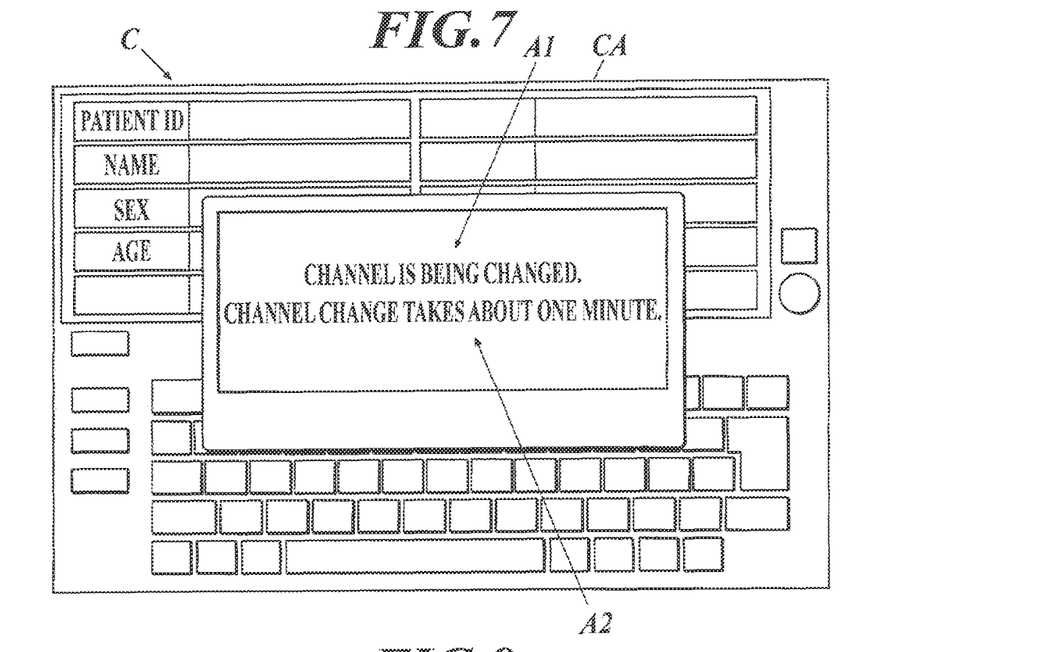
FIG. 7 illustrates an exemplary message appearing on a display device.

Alternatively, the elapsed time from the start of channel switching, for example, may be indicated in the form of, for example, a message or a progress bar (not shown), in place of the message A2 indicating the time t required to switch the channel (for example, one minute), as shown in FIG. 7, or together with the message A2. This configuration allows the operator to recognize how much more time it takes to switch the channel properly and readily.

As described above, the notifying device may indicate that the channel is under the switching operation in the form of a message on the screen CA. Alternatively, the notifying device may indicate it in the form of sound or vibration (in particular, if the mobile terminal (see FIG. 6) is a display device C integrated with the notifying device), as described above, together with or in place of the message.

Keeping on making a sound or generating vibration for about one consecutive minute during which the channel switch controlling device 62 is switching the channel, as described above, may hinder the operations of the operator or radiological technician. To avoid the problem, the notifying device may make a sound or generate vibration for only a predetermined period of time from the detection of radio interference by the channel interference detecting device 61. After the stop for a while, the notifying device resumes making a sound or generating vibration at the completion of channel switching by the channel switch controlling device 62.

In this case, the way in which the notifying device makes a sound or generates vibration at the completion of channel switching by the channel switch controlling device 62 may be different from that at the detection of radio interference by the channel interference detecting device 61 to facilitate distinction between them. This configuration allows the operator or radiological technician to distinguish the detection of radio interference by the channel interference detecting device 61 from the completion of channel switching.

Advantageous Effects

As described above, the channel switch controlling device 62 switches the channel when the channel interference detecting device 61 detects radio interference or interference waves from a predetermined radar, such as a weather radar. The radiographic image capturing system 100 according to this embodiment allows the notifying device to send a message to the screen CA of the display device C, makes a sound, or generates vibration during channel switching to notify an operator or radiological technician that the channel is under the switching operation. This configuration allows the operator or radiological technician to properly recognize that the channel is being switched.

As described above, the display device C displays a radiographic image p or radiographic image ppre for preview, which are generated based on the signal values D or signal values Dpre for preview transferred from the radiographic image capturing apparatus 1. The display device C is always used by the operator or radiological technician during imaging. Accordingly, if the notifying device is integrated with the display device C always used in imaging, notification of currently-executed channel-switching is properly sent to operator and the operator, who can properly recognize that the channel is being switched.

Upon occurrence of radio interference in the radiographic image capturing system 100, as shown in FIG. 4 or 5, for example, the radiographic image capturing system 100 suspends transfer of the signal values D from the radiographic image capturing apparatus 1 and switches the channel used for the transfer. Meanwhile, the operator or radiological technician does not know the reason for the suspension of the transfer of the signal values D, is hindered in his/her work, mistakenly believes that the cause of the suspension lies in a defect of the system, and may perform an unnecessary operation or processing. The radiographic image capturing system 100 can effectively prevent such an unnecessary operation or processing to ensure that imaging operations are performed properly.

Variations

As described above, the notifying device in the radiographic image capturing system 100 according to this embodiment informs the operator or radiological technician of a channel under a switching operation so that the operator or radiological technician can properly recognize that the channel is being switched. Different variations are available to ensure that the operator or radiological technician can recognize the channel switching properly.

In the following description, the notifying device sends a message to the screen CA of the display device C (see FIGS. 4 to 6) to notify the operator or radiological technician of the switching. Alternatively, the notifying device may make a sound or generate vibration (if the display device C is a mobile terminal (see FIG. 6), in particular), in place of or together with the message or is separated from the display device C, as described above.

Variation 1

Figure 8:
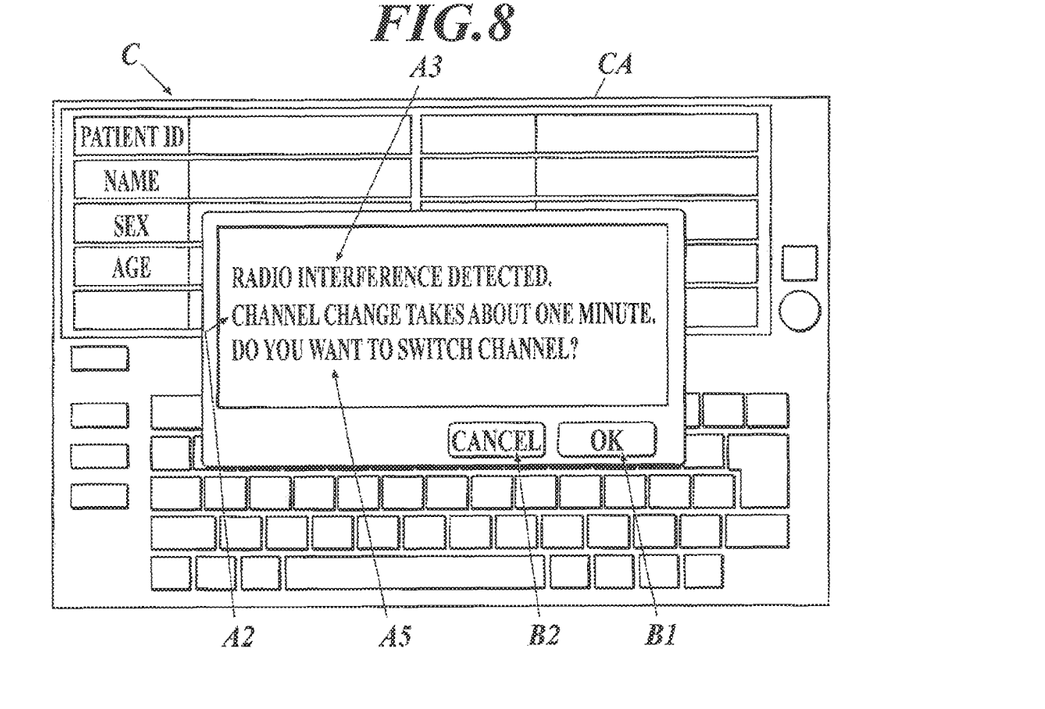
FIG. 8 illustrates another exemplary message appearing on the display device.
Figure 9:
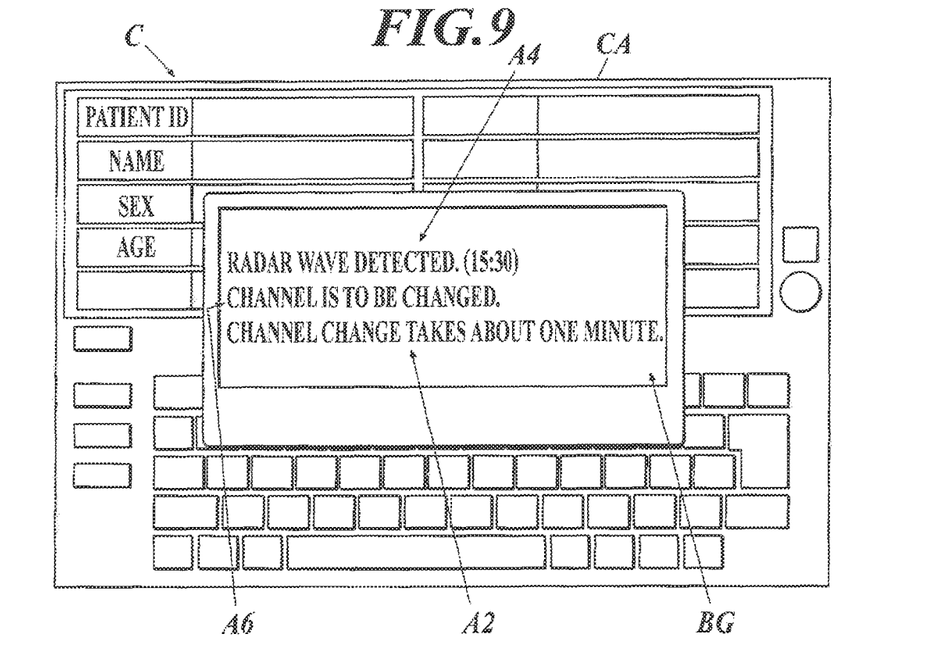
FIG. 9 illustrates another exemplary message appearing on the display device.

In response to reception of an interference detection signal from the channel interference detecting device 61 after detection of radio interference, the notifying device may display a message A3 indicating the detection of radio interference on the screen CA of the display device C to inform the operator of such detection, as shown in FIG. 8. In response to reception of a DFS detection signal from the channel interference detecting device 61 after detection of interference waves from a predetermined radar, such as a weather radar, the notifying device may display a message A4 indicating the detection of radar waves on the screen CA to inform the operator of such detection, as shown in FIG. 9.

These configurations allow the operator or radiological technician to properly confirm the occurrence of radio interference (message A3) or the detection of interference waves from a predetermined radar, such as a weather radar (message A4).

Variation 2

In response to the detection of radio interference by the channel interference detecting device 61, the operator or radiological technician may generate a radiographic image p based on the signal values D transferred from the radiographic image capturing apparatus 1. In this case, signal values D should preferably be transferred from the radiographic image capturing apparatus 1 to the console C as early as possible by switching the channel. Accordingly, the operator will instruct to switch the channel.

In the case where the detection of radio interference, the operator or radiological technician may prepare imaging of the next patient, it takes time to receive the next patient in the imaging room RA (see FIG. 4) or move the medical cart 70 to the sickroom R1 (see FIG. 5). Accordingly, the operator may determine channel switching to be unnecessary because the operator does not need to hurry up in transferring signal values D from the radiographic image capturing apparatus 1 to the console C.

For example, the data volume of signal values Dpre for preview transferred from the radiographic image capturing apparatus 1 to the display device C is smaller than that of all the signal values D, as described above (see FIG. 3). In response to the detection of radio interference at the channel interference detecting device 61, the operator or radiological technician may prefer immediate transfer of the signal values Dpre for preview in the current channel to transfer after the channel switching for about one minute because the operator can determine the channel switching to be unnecessary due to earlier transfer of the signal values Dpre for preview transfer.

As described above, the operator or radiological technician may determine the channel switching to be necessary or unnecessary, depending on the case, in response to the detection of radio interference by the channel interference detecting device 61. The display device C according to the above embodiment sends an instruction signal for channel switching to the channel switch controlling device 62 to switch the channel immediately after the display device C receives an interference detection signal from the channel interference detecting device 61. Alternatively, the display device C according to this variation may have the following configuration:

In response to the detection of radio interference at the channel interference detecting device 61, the notifying device displays a message A3 indicating the detection of radio interference on the screen CA of the display device C to informs the operator of the detection of radio interference, as shown in FIG. 8, while the display device C displays a message A5 "DO YOU WANT TO SWITCH CHANNEL?" to ask the operator or radiological technician for a decision.

In response to the reception of an instruction signal for channel switching from the operator or radiological technician (i.e., click of an "OK" button icon B1 in FIG. 8, for example), the display device C may send a switching signal to the channel switch controlling device 62.

In response to the reception of an instruction signal for non-channel switching from the operator or radiological technician (i.e., click of a "Cancel" button icon B2 in FIG. 8, for example), the display device C does not send a switching signal to the channel switch controlling device 62.

This configuration allows the display device C to switch or not switch the channel in line with the decision of the operator or radiological technician, thus increasing the usability of the radiographic image capturing system 100 for operators. The message A2 indicating the time t required to switch a channel (about one minute, for example), as shown in FIG. 8, allows the operator to determine the necessity for switching the channel in consideration of the time t required to switch the channel.

Variation 3

As described above, the IEEE802.11a standard requires to avoid interference over a wireless LAN through DFS on the detection of interference waves from a predetermined radar, such as a weather radar. In conformance with the standard, the channel interference detecting device 61 must switch the channel immediately after the detection of, not radio interference, but interference waves from a predetermined radar, such as weather radar.

In response to the reception of a DFS detection signal from the channel interference detecting device 61 after detection of interference waves from a predetermined radar, the display device C according to this embodiment sends an instruction signal for channel switching to the channel switch controlling device 62 to switch the channel immediately. When receiving the switching signal, the channel switch controlling device 62 switches the channel used for a wireless transfer of the signal values D from the radiographic image capturing apparatus 1, as described above.

This configuration allows the channel used for a wireless transfer of the signal values D from the radiographic image capturing apparatus 1 to be switched to another channel immediately after the detection of interference waves from a predetermined radar, such as a weather radar, at the channel interference detecting device 61, thus properly avoiding interference between interference waves from a predetermined radar and signal values D transferred from the radiographic image capturing apparatus 1.

Unlike the detection of radio interference at the channel interference detecting device 61 in Variation 2, the detection of interference waves from a predetermined radar at the channel interference detecting device 61 in Variation 3 allows the display device C to transmit a switching signal to the channel switch controlling device 62 without asking the operator or radiological technician for a decision, in response to the reception of a DFS detection signal from the channel interference detecting device 61.

In response to the detection of interference waves from a predetermined radar at the channel interference detecting device 61, the notifying device displays a message A4 "RADAR WAVE DETECTED" or a message A6 "CHANNEL IS TO BE CHANGED" (together with the message A2 indicating the time t required to switch a channel (about one minute, for example)) on the screen CA of the display device C, as shown in FIG. 9, as described above. To reinforce the recognition of the operator or radiological technician that the channel is to be switched, without asking the operator for a decision, the notifying device may, for example, display a background BG in yellow to call for attention of the operator.

In this case, neither "OK" button icon B1 nor "Cancel" B2 button icon (see FIG. 8) is displayed, as shown in FIG. 9, because the notifying device does not need to ask the radiological technician for a decision, as described above.

Variation 4

Variations 1 to 3 (see FIGS. 8 and 9) relates to the messages A3 to A6 displayed at the start of channel switching. The above embodiment (see FIG. 7) relates to the message A1 during channel switching. The notifying device according to the above embodiment may make a sound or generate vibration upon completion of channel switching at the channel switch controlling device 62, as described above.

Figure 10:
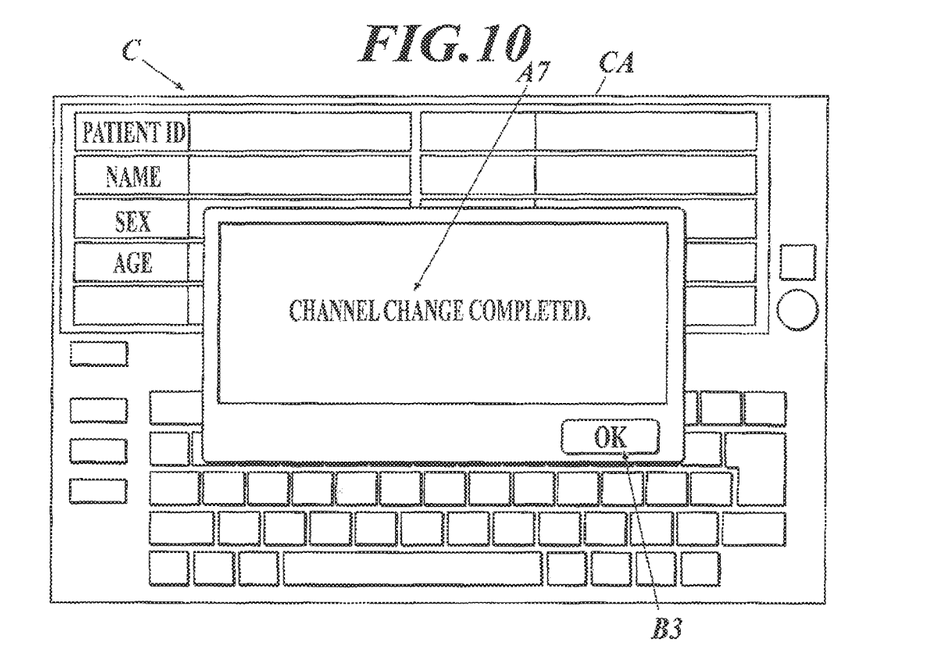
FIG. 10 illustrates another exemplary message appearing on a display device.

In response to the completion of channel switching by the channel switch controlling device 62, for example, the notifying device sends a message A7 "CHANNEL CHANGE COMPLETED" to the screen CA of the display device C, as shown in FIG. 10, to notify the operator or radiological technician of the completion of channel switching. Alternatively, the notifying device may make a sound or generate vibrations, as described above.

This configuration allows the operator or radiological technician, who watches the message A7 on the screen CA of the display device C, to properly recognize the completion of channel switching. An "OK" button icon B3 may appear, as shown in FIG. 10, to prompt the operator to click it. This configuration further reinforces the recognition of the completion of channel switching.

In the above embodiment and variations, the channel interference detecting device 61 sends an interference detection signal and/or a DFS detection signal to the display device C, and the display device C sends a switching signal to the channel switch controlling device 62, as needed. In other words, the switching signal is sent in line with the decision of the operator or radiological technician upon the detection of radio interference, whereas the switching signal is sent unconditionally upon the detection of interference waves from a predetermined radar, such as a weather radar. Alternatively, the channel interference detecting device 61 and the display device C may have any other configuration.

The above embodiment and variations have been described, but they should not be construed to limit the present invention, and various modifications may be made without departing from the scope of the invention.

What is claimed is:

1. A radiographic image capturing system comprising:
    a radiographic image capturing apparatus with radiation detecting elements, wherein the radiographic image capturing apparatus wirelessly transfers a signal value read from the radiation detecting elements;
    a channel interference detecting device adapted for detecting radio interference; and
    a notifying device which gives a notice to an operator who operates the radiographic image capturing system, wherein
    when the channel interference detecting device detects the radio interference, the notifying device notifies the operator that the radio interference is detected.

2. The radiographic image capturing system according to claim 1, wherein
    the channel interference detecting device measures a radio interference level, and
    the notifying device notifies the operator that the radio interference is detected when the radio interference level reaches a predetermined threshold or greater.

3. The radiographic image capturing system according to claim 2, wherein the channel interference detecting device measures the radio interference level at each of channels that include a channel being used and another channel.

4. The radiographic image capturing system according to claim 3, further comprising a display device that displays, for each of the channels, the radio interference level at each of the channels measured by the channel interference detecting device.

5. The radiographic image capturing system according to claim 3, further comprising a channel switch controlling device that switches the channel being used to the another channel having a lower radio interference level based on the radio interference level at each of the channels measured by the channel interference detecting device.

6. The radiographic image capturing system according to claim 5, wherein the notifying device notifies the operator that the channel being used is being switched when the channel switch controlling device switches the channel being used.

7. The radiographic image capturing system according to claim 1, wherein the channel interference detecting device detects interference with a radio wave from a predetermined radar required to avoid interference through dynamic frequency selection.

8. The radiographic image capturing system according to claim 1, wherein a medical cart is provided with the channel interference detecting device and the notifying device.

* * * * *